United States Patent [19]

Frye

[11] 4,327,326
[45] Apr. 27, 1982

[54] AUTOMATIC TESTING SYSTEM FOR ELECTRIC NERVE STIMULATOR UNITS

[75] Inventor: George J. Frye, Portland, Oreg.

[73] Assignee: Frye Electronics, Inc., Tigard, Oreg.

[21] Appl. No.: 150,332

[22] Filed: May 16, 1980

[51] Int. Cl.³ .................... G01R 31/00; G01R 11/00
[52] U.S. Cl. ................................. 324/158 R; 324/142
[58] Field of Search ............... 324/158 R, 142, 73 R, 324/76 R

[56] References Cited

U.S. PATENT DOCUMENTS 4,217,545 8/1980 Kusui et al. .................... 324/142

Primary Examiner—Ernest F. Karlsen
Attorney, Agent, or Firm—Adrian J. LaRue

[57] ABSTRACT

An automatic testing system for electric nerve stimulator units is described wherein a digital computer controller utilizing programmable read only memory is used to control testing transcutaneous electrical nerve stimulator (TENS) units, such tests being conducted by sensing the output pulses from the stimulator under test and processing the output pulse signal information by circuit means under the control of the computer resulting in digital readouts of the peak output voltage, width and rate of the output pulses of the stimulator. The load impedance and quantity of delivered pulse charge for a patient can also be determined as digital readouts and indications of the pulse polarity and/or bipolarity is displayed.

17 Claims, 5 Drawing Figures

AUTOMATIC TESTING SYSTEM FOR ELECTRIC NERVE STIMULATOR UNITS

BACKGROUND OF THE INVENTION

Transcutaneous electric nerve stimulator (TENS) units are used by persons to block pain transmitted by the nervous system. These devices generate electrical pulses having a peak output voltage, pulse width and pulse rate. The pulses are transmitted to electrodes which are positioned on a person's body depending on the location of the pain. The amplitude of the pulses is adjustable to a level that will minimize the pain. Different people have different sensitivity thresholds to pain and stimulation.

Testing of the TENS units is important to determine whether the units are functioning properly in order to separate the person's subjective pain problems from possible difficulties with the units themselves. Such testing has not been routinely undertaken heretofor because of the lack of properly designed testing equipment.

SUMMARY OF THE INVENTION

The present invention relates to testing systems and more particularly to automatic testing systems for testing electric nerve stimulating units preferably of the transcutaneous variety.

The present invention is realized by connecting the output of a stimulator unit to the automatic testing system and connecting the electrodes from the automatic testing system to the person on whom the stimulator is to be fitted. The system can then be used to make measurements of the output signal parameters of the stimulator under test by use of an internal load built into the test system, or it can be used to make measurements of the output signal parameters of a stimulator under test as well as a measurement of the electrode impedance of the electrodes as connected to the person and of the charge delivered by the stimulator to that person.

The output of the stimulator under test is sensed by signal sensing means which generate output signals related to the voltage and current of the stimulator's output pulses. The voltage output signal is detected to determine its peak value and that information is used to control a circuit that produces an output signal equal to the width of the stimulator's output voltage pulses. This output signal is used to control the operation of a number of signal gating means which receive the voltage and current signals related to the stimulator's output pulses to make measurements of the various parameters of interest. The signals derived from the signal gating means are used to deliver charge and digital information to integrator and flip flop means. Signals from the integrator means are converted into digital information form by analog to digital converter means, which digital information is processed by a digital computer means. Signals from the flip flop means are used directly by the digital computer means. The digital computer means processes the information from the integrator means and the flip flop means to generate digital signals to operate display means and/or printer means to display and/or print the measured parameters.

An object of the present invention is to provide a testing system for testing electric stimulator units for use on a person's body to relieve pain.

Another object of the present invention is the provision of a testing system for automatically testing electrical stimulator units.

A further object of the present invention is to provide an automatic testing system for testing a stimulator unit in operation on a person.

An additional object of the present invention is the provision of an automatic testing system for testing a stimulator unit without being connected to a person.

Still a further object of the present invention is to provide an automatic testing system utilizing computer control for maximum flexibility of test procedures.

A still further object of the present invention is the provision of a unique differential input amplifier circuit as part of the test system.

A still further object of the present invention is to provide a novel peak detector circuit as part of the test system.

These and other objects and advantages of the present invention will become apparent from the following description when taken in conjunction with the accompanying drawings. It is to be understood that variations of the present invention can be made without departing from the scope of the invention as defined herein.

DETAILED DESCRIPTION OF THE INVENTION

Figure 1:
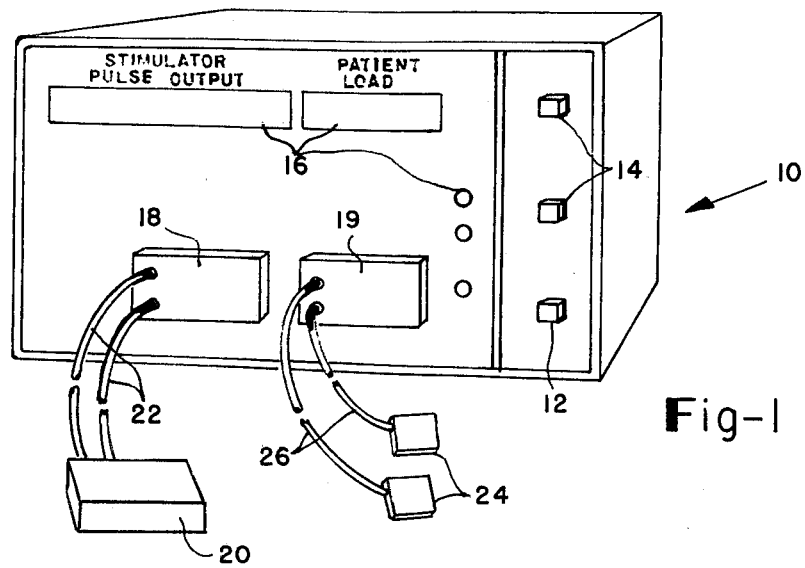
FIG. 1 is a frontal perspective view showing the overall outward appearance of the automatic stimulator testing system.

Turning now to FIG. 1, a housing 10 is shown which houses the electronic circuitry of the automatic stimulator testing system, and which contains power switch 12, control switches 14, display means 16, and connector block means 18. A stimulator 20 to be tested is connected to connector block means 18 via electrical leads 22 and patient electrodes 24 are connected via electrical leads 26 to connector block means 19.

Figure 3:
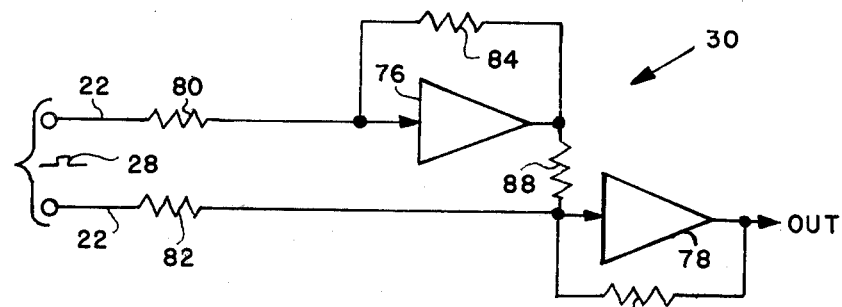
FIG. 3 is a schematic diagram of the differential input amplifier circuit.
Figure 2:
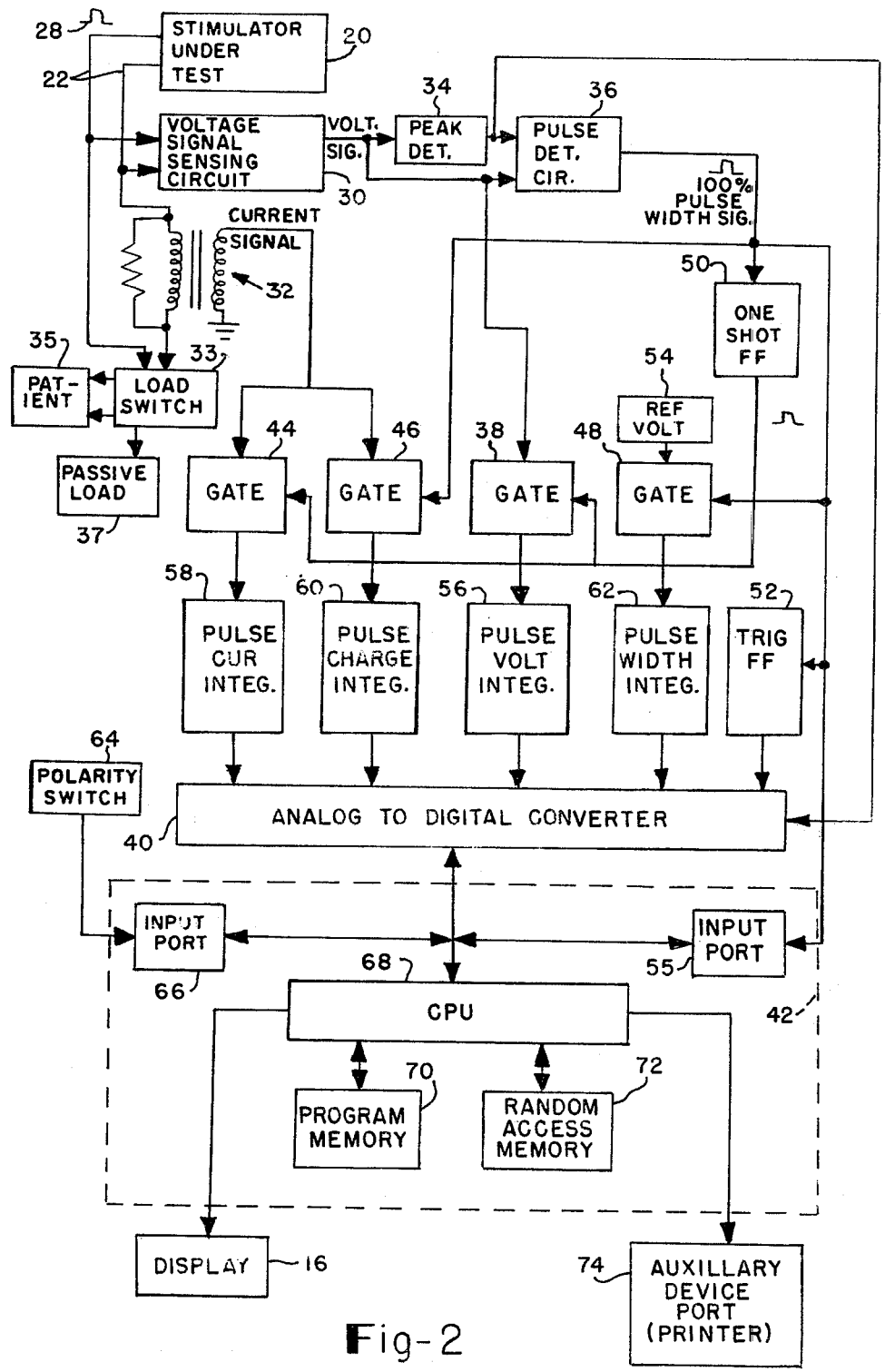
FIG. 2 is a block diagram of the automatic stimulator testing system.

FIG. 2 shows a block diagram of the automatic stimulator testing system as connected to a stimulator 20. The output pulses 28 from stimulator 20 under test are received via leads 22 by a voltage signal sensing circuit 30 which comprises a differential amplifier as illustrated in FIG. 3 which will be described in greater detail later, and also by current signal sensing transformer 32 of conventional design. The output pulses 28 are then transmitted to load switch 33 of conventional design as one of control switches 14 and from there to either a patient 35 or to passive load 37 which consists of a conventional RC circuit network.

Figure 4:
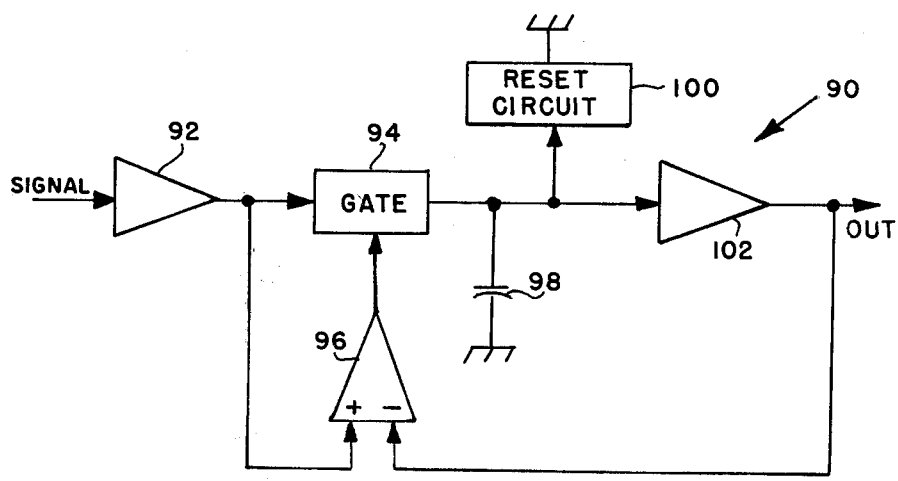
FIG. 4 is a schematic diagram of the peak detector circuit.

The output from voltage signal sensing circuit 30 is transmitted to peak detector 34 which is illustrated in FIG. 4 and will be described in greater detail hereafter, and also to pulse detection circuit 36 and gate 38. Peak detector 34 provides an output signal which is equal to the peak voltage (plus or minus) of the voltage signal from the voltage signal sensing circuit 30. Pulse detection circuit 36 is of conventional design and its sense levels are controlled by the output from peak detector 34. Peak detector 34 also provides an output signal to a conventional analog to digital converter 40 for conversion to a digital signal for use by computer 42.

The output from current signal sensing transformer 32 is a voltage waveform which corresponds to the current amplitude of the stimulator pulse signal 28 and it is connected to gates 44 and 46.

Pulse detection circuit 36 generates a binary output signal that has a pulse width that corresponds to the pulse width of the voltage signal from the voltage signal sensing circuit 30. The output from pulse detection circuit 36 directly drives gates 46 and 48, is used to trigger one shot flip flop 50 and triggered flip flop 52, and is also connected to input port 55. The output from one shot flip flop 50 is of a short constant width duration and is transmitted to drive gates 38 and 44. Gates 38, 44, 46, 48, one shot flip flop 50 and triggered flip flop 52 are of conventional design. A reference voltage source 54 is connected to gate 48. The output of gate 38 is connected to pulse voltage integrator 56; the output from gate 44 is connected to pulse current integrator 58; the output from gate 46 is connected to pulse charge integrator 60 and the output from gate 48 is connected to pulse width integrator 62. Integrators 56, 58, 60 and 62 are of conventional design.

When gate 48 connects reference voltage 54 to pulse width integrator 62 by action of the output from pulse detection circuit 36, a voltage is generated at the output of pulse width integrator 62 which is proportional to the pulse width of the stimulator signal 28.

When gate 46 connects the current signal from current signal sensing transformer 32 to pulse charge integrator 60 by action of the output pulse detection circuit 36, a voltage is generated which is proportional to the charge delivered to the load by the stimulator signal 28. The load may be chosen to be either patient 35 or passive load 37 via load switch 33.

When gate 38 connects the voltage signal from voltage signal sensing circuit 30 to pulse voltage integrator 56 by action of the output of one shot flip flop 50, a voltage is generated which is proportional to the voltage of the stimulator signal 28 during the first part of the stimulator's output waveform. This proportional voltage forms the first part of the information necessary to derive a load impedance measurement.

When gate 44 connects the current signal from current signal sensing transformer 32 by action of the output of one shot flip flop 50, a voltage is generated which is proportional to the current of the stimulator signal 28 during the first part of the stimulator's output waveform. This proportional voltage forms the second part of the information necessary to derive the load impedance measurement. The second part of information divided into the first part of information yields load impedance information.

The output signals from integrators 56, 58, 60, and 62 are transmitted to analog to digital converter 40, where these signals are coded into digital format for use by the computer 42.

Triggered flip flop 52 receives an input signal from pulse detection circuit 36. Its function is to remember if an input signal was received or not. Its output is connected to the analog to digital converter 40 and provides information to the computer 42 for subsequent use.

Input port 55 by being connected to pulse detection circuit 36 allows the computer 42 to determine whether or not a pulse signal 28 is present.

Polarity switch 64 is one of control switches 14 and is connected to input port 66 and provides information to computer 42 as to whether or not the operator wishes to change the examination of the input pulse 28 from one polarity to the other.

Computer means 42 comprises CPU 68, program memory 70, random access memory 72 and input ports 55 and 66. The CPU 68 is typically a conventional microprocessor such as an Intel 8080 or the like. Program memory 70 is typically a conventional programmable read only memory (PROM) such as an Intel 2716 or the like. Random access memory 72 (RAM) is typically a conventional integrated circuit such as a pair of Intel 2114's or the like. Input ports 55 and 66 are typically conventional integrated circuits such as RCA 4043's or the like.

Figure 5:
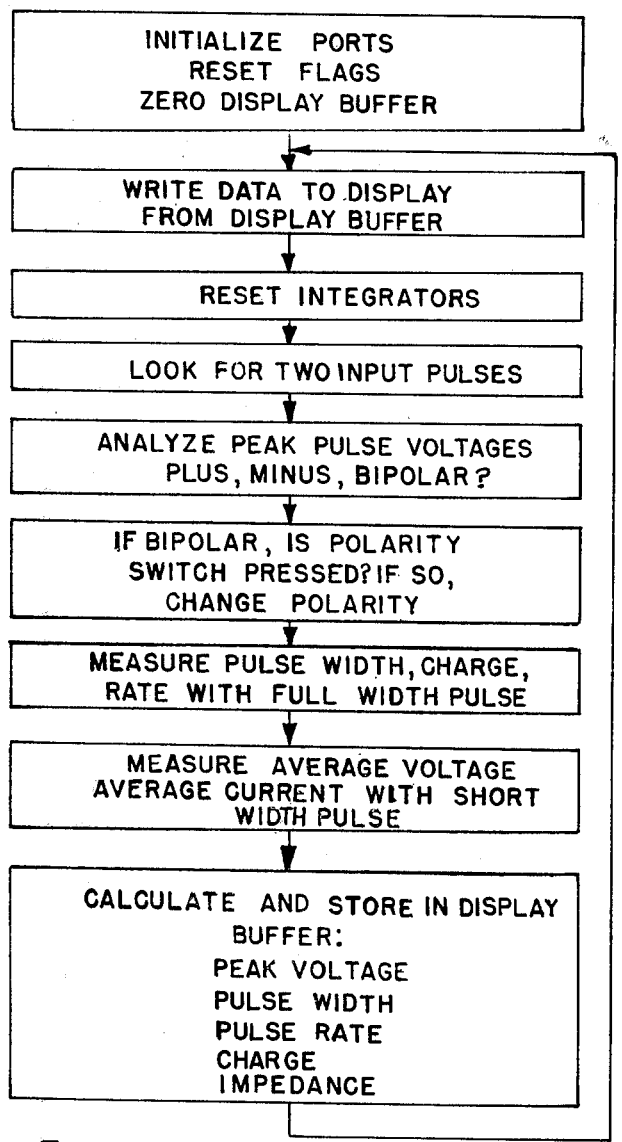
FIG. 5 is a flow chart of the digital computer program for automatically processing the sensed stimulator output signals.

The CPU 68 follows instructions contained in program memory 70 as outlined in the flow chart of FIG. 5, and stores information in random access memory 72. It also receives information from input ports 55 and 66 and from analog to digital converter 40.

Computer 42 also provides control signals connected to the integrators 56, 58, 60 and 62, peak detector 34, and to triggered flip flop 52, for purposes of reset.

Computer 42 operates display means 16 in the form of digital display means to provide digital information of the pulse signal 28 including peak output voltage, pulse width, pulse rate, load impedance and delivered charge. Computer 42 also operates display means 16 in the form of indicator lights to provide information of the polarity and bipolarity of pulse signal 28.

If desired, computer 42 can provide operational information to auxiliary device port 74 in order to operate a printer or other similar devices for making permanent copies of the displayed information or for connection to a control device such as a computer terminal.

Reference is made to FIG. 5 which illustrates a flow diagram for operation of digital computer 42. A person skilled in the art can readily discern from examination of the flow diagram the operation of the computer 42.

Reference is made to FIG. 3 regarding the differential amplifier circuit which comprises voltage signal sensing circuit 30 of FIG. 2. Signal 28 on leads 22 is transmitted to conventional operational amplifier's 76 and 78 via resistors 80 and 82, which are of equal value. The output of the operational amplifier 76 is connected to the input of operational amplifier 78 via resistor 88.

Input signal 28 causes currents to flow in resistors 80 and 82. Operational amplifiers 76 and 78 respond to these currents with voltage outputs set by resistors 84 and 86, respectively. The output of operational amplifier 76 also causes a current to flow in resistor 88 which causes operational amplifier 78 to generate an output signal. The total response of operational amplifier 78 is formed by the sum of the responses from input currents received from resistors 82 and 88. If resistors 80 and 82 are of equal value, and if resistors 84, 86 and 88 are of equal value, but of a value which may be different from that of 80 and 82, then the voltage appearing at the output of operational amplifier 78 will consist of a signal proportional to the differential signal appearing on leads 22.

Referring now to FIG. 4, peak detector circuit 90 comprises one half of peak detector 34 of FIG. 2, and is designed to process the positive going pulse voltage signal from voltage signal sensing circuit 30 of FIG. 2. Peak detector circuit 90 includes a conventional buffer amplifier 92 which receives the pulse voltage input signal and produces a substantially identical output voltage which is then transmitted to input signal terminal of conventional gate 94 and the positive terminal of conventional high gain differential amplifier 96. Gate 94 has a finite resistance in its conductive mode. The storage capacitor 98 is connected to the output signal terminal of gate 94, the input signal terminal of reset circuit 100 and to the input of conventional buffer amplifier 102. The output of buffer amplifier 102 is connected to the negative input terminal of high gain differential amplifier 96 and also provides an output signal.

The output of differential amplifier 96 is controlled by the relative voltages present at the output of buffer amplifier 92 and on the storage capacitor 98. Buffer amplifier 102 transfers the voltage level on the storage capacitor 98 to the negative input of differential amplifier 96. When the voltage present at the output of buffer amplifier 92 is more positive than the voltage present at the output of the buffer amplifier 102, then the output of the differential amplifier goes positive and the gate 94 is caused to conduct. Capacitor 98 now charges to the same potential as that present at the output of buffer amplifier 92. When the voltage present at the output of buffer amplifier 92 swings negative with respect to that present at the output of the buffer amplifier 102, then the output of differential amplifier 96 swings negative, causing the gate 94 to stop conduction. The finite resistance of gate 94 allows small potential differences to exist between the buffer amplifier 92 and storage capacitor 98 during charging and discharging of capacitor 98. The voltage on capacitor 98 and therefore the voltage present at the output of buffer amplifier 102 thus are set at the most positive level of the signal present at the input of buffer amplifier 92. Buffer amplifier 102 may be omitted in some designs. The reset circuit 100 may consist of one of several conventional circuit configurations, including a semiconductor gate or a resistor.

It is to be noted that the automatic stimulator testing system can be used to conduct tests on a stimulator unit during the time when the unit is connected to a person and is in operation. The testing system automatically processes the signals being generated by the stimulator unit to display digital readouts of the peak voltage, width and rate of these signals. The load impedance and quantity of delivered pulse charge for a patient can also be displayed as digital readout information. Moreover, the pulse polarity and/or bipolarity of the stimulator signals can be indicated.

If desired, a stimulator unit can be tested to determine its operational characteristics or if it is properly operating without being connected to a person by use of an impedance load in passive load 37 which is representative of a person.

An important feature of the automatic stimulator testing system of the present invention is that it automatically conducts tests on a stimulator unit while in operation whether connected to or not connected to a person and automatically displays readout information of the operational characteristics of the stimulator. Thus, the principal purpose of the testing system is to monitor the amplitudes and durations of the output signals from a stimulator unit, but to supply no signals, DC or pulsating, to the person or load from the testing system itself.

Although the invention has been described hereinbefore with respect to the foregoing imbodiments, it is to be appreciated that various changes and modifications may be made therein without departing from the scope of the invention as set forth in the accompanying claims.

The invention is claimed in accordance with the following:

1. An automatic stimulator testing system, comprising in combination:
   signal sensing circuit means for sensing signals generated by a stimulator and generating voltage and current output signals representative of the stimulator generated signals;
   gate means for receiving said voltage and current output signals;
   peak detector means for receiving said voltage output signals and generating output signals equal to the peak voltage of said voltage output signals;
   detection circuit means for receiving said output signals from said peak detector means and said voltage output signals from said signal sensing circuit means, said detection circuit means generating output pulses in the form of gate driving signals corresponding to the width of said voltage output signals and transmitting said gate driving signals to said gate means;
   integrator means connected to said gate means for receiving said voltage and current output signals when said gate means are operated by said gate driving signals, said integrator means generating converter signals representative of the average of said voltage and current output signals during the time said gate driving signals are present;
   analog to digital converter means for receiving said converter signals and said output signals from said peak detector means, all of said signals being converted into digital signals thereby;
   digital computer means for receiving said digital signals, for controlling said integrator means and said peak detector means and for processing said digital signals; and
   display means connected to said digital computer means for displaying information of the stimulator generated signals.

2. An automatic stimulator testing system according to claim 1 wherein one shot flip flop means receives said output signals from said detection circuit means and is triggered thereby to generate short constant width duration signals to drive some of said gate means.

3. An automatic stimulator testing system according to claim 1 wherein a reference voltage is connected to one of said gate means.

4. An automatic stimulator testing system according to claim 1 wherein switch means is provided for connecting the stimulator to a person or to a passive load representative of a person.

5. An automatic stimulator testing system according to claim 1 wherein said display means includes indicator means connected to said digital computer means for indicating polarity and/or bipolarity of the stimulator-generated signals.

6. An automatic stimulator testing system according to claim 5 wherein switch means is connected to said digital computer means for changing polarity of the examination of the stimulator-generated signals.

7. An automatic stimulator testing system according to claim 1 wherein triggered flip flop means receives the output pulses from said detection circuit means and provides an input signal to said analog to digital converter means after the occurance of one of the said output pulses.

8. An automatic stimulator testing system according to claim 1 wherein control means or printing means is connected to said digital computer means for providing control signals to said digital computer means or for printing information, including the information displayed by said display means.

9. An automatic stimulator testing system, comprising in combination:

signal sensing circuit means for sensing signals generated by a stimulator and generating voltage and current output signals representative of the stimulator-generated signals;

gate means for receiving said voltage and current output signals;

detector circuit means for receiving said voltage output signals and for generating output pulses providing gate driving signals;

integrator means for receiving said voltage and current output signals when said gate means are operated by said gate driving signals and for generating converter signals representative of the average value of the voltage and current signals during the operation time of said gate driving signals;

analog to digital converter means for receiving said converter signals and said output pulses from said detector circuit means and for generating digital signals representative of the average of said voltage and current output signals and of said voltage and current output signals;

digital computer means for receiving said digital signals, for processing said digital signals for generating display signals and for controlling said integrator means and said detector circuit means; and display means for receiving said display signals and operating said display means for displaying information of the stimulator-generated signals.

10. An automatic stimulator testing system according to claim 9 wherein said detector circuit means comprises peak detector means for receiving said voltage output signals and for generating output signals representative of the peak voltage of said voltage output signals and detection circuit means for receiving said output signals from said peak detector means and said voltage output signals from said signal sensing circuit means and for generating said output pulses.

11. An automatic stimulator testing system according to claim 10 wherein one shot flip flop means receives said output pulses and is triggered thereby to generate short constant width duration signals to drive some of said gate means.

12. An automatic stimulator testing system according to claim 9 wherein a reference voltage is connected to one of said gate means.

13. An automatic stimulator testing system according to claim 9 wherein switch means is provided for connecting the stimulator to a person or to a passive load representative of a person.

14. An automatic stimulator testing system according to claim 9 wherein said display means includes digital readout means for digitally displaying peak output voltage, width, rate, delivered charge and load impedance of the stimulator-generated signals.

15. An automatic stimulator testing system according to claim 9 wherein said display means includes indicator means for indicating polarity and/or bipolarity of the stimulator-generated signals.

16. An automatic stimulator testing system according to claim 9 wherein switch means is provided for changing examination of the polarity of the stimulator-generated signals.

17. An automatic stimulator testing system according to claim 9 wherein triggered flip flop means receives the output pulses of said detector circuit means and provides an input signal to said analog to digital converter means after reception of an output pulse by said flip flop means.

* * * * *